(12) United States Patent
Roorda

(10) Patent No.: US 10,045,943 B2
(45) Date of Patent: Aug. 14, 2018

(54) IMPLANTABLE MEDICAL DEVICES FOR EXTENDED RELEASE OF THERAPEUTIC AGENTS

(71) Applicant: NANO PRECISION MEDICAL, INC., Emeryville, CA (US)

(72) Inventor: Wouter Erik Roorda, Emeryville, CA (US)

(73) Assignee: Nano Precision Medical, Inc., Emeryville, CA (US)

( * ) Notice: Subject to any disclaimer, the term of this patent is extended or adjusted under 35 U.S.C. 154(b) by 22 days.

(21) Appl. No.: 15/094,936

(22) Filed: Apr. 8, 2016

(65) Prior Publication Data

US 2016/0220496 A1     Aug. 4, 2016

Related U.S. Application Data

(63) Continuation of application No. PCT/US2015/058449, filed on Oct. 30, 2015.

(60) Provisional application No. 62/074,052, filed on Nov. 2, 2014.

(51) Int. Cl.
| | |
|---|---|
| *A61K 9/48* | (2006.01) |
| *A61K 9/00* | (2006.01) |
| *A61K 47/34* | (2017.01) |
| *A61K 38/26* | (2006.01) |
| *A61K 38/22* | (2006.01) |
| *A61L 31/06* | (2006.01) |
| *A61L 31/14* | (2006.01) |
| *A61L 31/16* | (2006.01) |

(52) U.S. Cl.
CPC .......... *A61K 9/4808* (2013.01); *A61K 9/0024* (2013.01); *A61K 9/4866* (2013.01); *A61K 38/2278* (2013.01); *A61K 38/26* (2013.01); *A61K 47/34* (2013.01); *A61L 31/06* (2013.01); *A61L 31/148* (2013.01); *A61L 31/16* (2013.01)

(58) Field of Classification Search
CPC .................................................... A61K 9/0024
See application file for complete search history.

(56) References Cited

U.S. PATENT DOCUMENTS

| | | | |
|---|---|---|---|
| 2011/0106006 A1* | 5/2011 | Martin | A61K 9/0024 604/93.01 |
| 2011/0245162 A1 | 10/2011 | Fineman et al. | |
| 2014/0086972 A1 | 3/2014 | Martin et al. | |
| 2015/0273021 A1* | 10/2015 | Kaplan | A61K 47/42 514/7.2 |
| 2017/0281547 A1* | 10/2017 | Karavas | A61K 9/1647 |

FOREIGN PATENT DOCUMENTS

| | | |
|---|---|---|
| WO | 2008/061355 A1 | 5/2008 |
| WO | 2013/085951 A1 | 6/2013 |

OTHER PUBLICATIONS

Jain, R., The manufacturing techniques of various drug loaded biodegradable poly(lactide-co-glycolide)(PLGA) devices, Biomaterials, vol. 21, Iss 23, 2000, pp. 2475-2490.*
International Search Report; PCT/US2015/058449; dated Jan. 12, 2016.
Extended European Search Report, dated Mar. 29, 2018, 4 pgs.

* cited by examiner

*Primary Examiner* — Gina Chieun Yu Justice
(74) *Attorney, Agent, or Firm* — Kilpatrick Townsend & Stockton LLP

(57) ABSTRACT

The invention pertains to implantable medical devices for controlled delivery of therapeutic agents. Some devices according to the invention have a titanium reservoir, and a porous titanium oxide based membrane to control the rate of release of the therapeutic agent. The reservoir contains a formulation of the active agent, including a stabilizer for the active agent, wherein the stabilizer is provided in an extended release configuration.

18 Claims, 1 Drawing Sheet

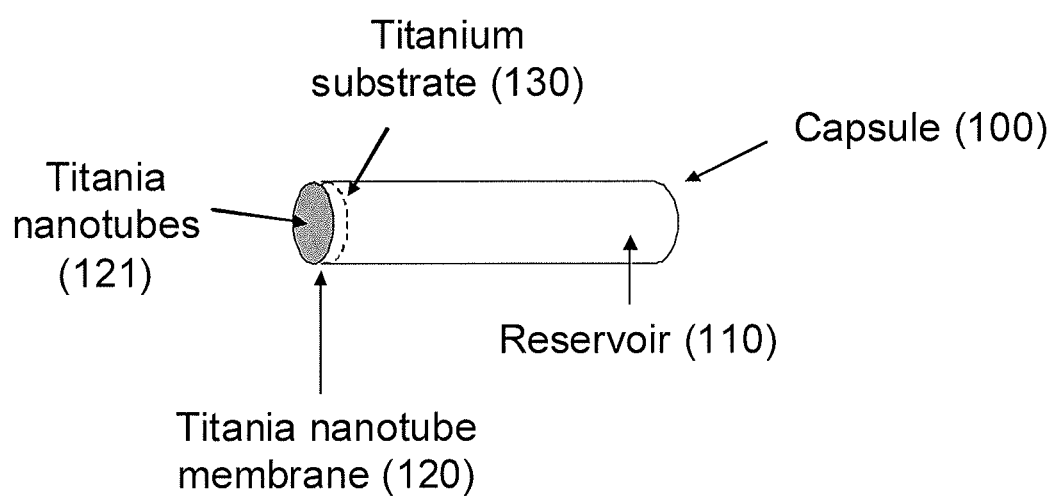

US 10,045,943 B2

IMPLANTABLE MEDICAL DEVICES FOR EXTENDED RELEASE OF THERAPEUTIC AGENTS

CROSS-REFERENCES TO RELATED APPLICATIONS

This application is a continuation of PCT/US2015/058449, filed Oct. 30, 2015, which application claims priority to U.S. Provisional Patent Application No. 62/074,052, filed Nov. 2, 2014, the disclosures of all of which are hereby incorporated by reference in their entireties for all purposes.

BACKGROUND OF THE INVENTION

Extended release of beneficial substances such as therapeutic agents from devices having a reservoir containing the beneficial substance requires adequate stability of the substance in the reservoir for the duration of the release. Therapeutic agents are typically more stable in solid form than in solution, and many reservoir devices contain therapeutic agents in solid form during most of the duration of release. Such devices include implants delivering highly hydrophobic agents, for instance hormone drugs used for birth control, and implantable osmotic pumps, such as those described in U.S. Pat. No. 8,052,996 incorporated herein by reference.

In contrast, some membrane-controlled devices for the extended release of hydrophilic drugs, such as peptides and proteins, rely on dissolution of the therapeutic agents in an aqueous environment to enable diffusion of the agent out of the reservoir. Therefore, such devices face the challenge of requiring the therapeutic agent to be in solution to be released, while at the same time the dissolved state of the therapeutic agent is prone to degradation.

Examples of devices requiring the therapeutic agent to be in solution include devices that are equipped with a nanotube-based membrane, such as described in U.S. Patent Application Pub. No. 2014/0371687 incorporated herein by reference. Extended release of therapeutic agents through nanotube-based membranes may be controlled by matching the dimensions of the nanotubes to the molecular dimensions of the therapeutic agent. However, especially in the case peptides and proteins, the therapeutic agents frequently have molecular dimensions significantly larger than those of their stabilizer molecules, leading to overly rapid and uncontrolled release of the stabilizer. Therefore, such devices face the unique challenge of providing stabilizers for therapeutic agents in a composition that avoids their overly rapid and uncontrolled release.

BRIEF SUMMARY OF THE INVENTION

In one embodiment, the present invention provides an implantable drug delivery system, the implantable drug delivery system comprising:
 a capsule suitable for implantation;
 a reservoir encapsulated by the capsule, wherein the reservoir contains a pharmaceutical composition including a therapeutic agent and a stability enhancing agent; and
 at least one nanoporous membrane in fluid contact with the reservoir; wherein the stability enhancing agent is provided in an extended release configuration.

In another embodiment, the present invention provides a method for treating a disease in a subject in need thereof, administering to the subject a therapeutically effective amount of a therapeutic agent contained within an implantable drug delivery system, the drug delivery system including:
 a capsule suitable for implantation;
 a reservoir encapsulated by the capsule, wherein the reservoir contains a pharmaceutical composition comprising the therapeutic agent and a stability enhancing agent; and
 at least one nanoporous membrane in fluid contact with the reservoir, wherein the stability enhancing agent is provided in an extended release configuration.

In still another embodiment, the present invention provides a pharmaceutical composition, the pharmaceutical composition comprising:
 a therapeutic agent; and
 a stability enhancing agent.

These and other aspects, objects and embodiments will become more apparent when read with the detailed description and FIGURE which follow.

BRIEF DESCRIPTION OF THE DRAWING

The FIGURE shows one embodiment of an implantable device useful in present invention.

I. DEFINITIONS

"Therapeutic agent" refers to any agent capable of providing a therapeutic response, such as a drug or biologic.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Membrane" refers to a porous structure allowing diffusion of molecules from one side of the structure to the other through the structure.

"Titania nanotube membrane" refers to an array of titania nanotubes on a titanium substrate where at least a portion of the titania nanotubes are open at both ends and capable of allowing diffusion of liquids or solids from one side of the membrane to the other through the titania nanotubes.

"Extended release configuration" means that the stability enhancing agent or stabilizer provides long-term stability through an extended release mechanism. These mechanisms include, but are not limited to, biodegradation, erosion, dissolution, hydrolysis, lysis, enzymatic cleavage, proteolytic cleavage, etc.

"Fluid contact" refers to the contents of the reservoir being able to be released or diffuse from the reservoir through a membrane.

"Aspect ratio" refers to the ratio of length to diameter of the titania nanotubes, including the internal and external diameter.

"Zero-order rate of release" refers to the rate of release that is independent of concentration of the therapeutic agent in the reservoir.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, The Art, *Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Diabetes" or "diabetes mellitus" refers to the group of metabolic diseases having raised blood sugar levels for an extended period of time. Diabetes includes type 1 diabetes, resulting from a lack of insulin production, and type 2 diabetes, which results from insulin resistance where the cells no longer respond to insulin and can progress to a lack of insulin. Other forms of diabetes are known to one of skill in the art.

"Acid" refers to a compound that is capable of donating a proton ($H^+$) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids.

"Base" refers to a compound capable of accepting a proton ($H^+$) under the Bronsted-Lowry definition, or is an electron pair donor under the Lewis definition. Representative bases include, but are not limited to, hydroxy, alkylhydroxy, amines (—NRR), alkylamine, arylamine, amide (—C(O)NRR), sulfonamide (—S(O)$_2$NRR), phosphonamide (—P(O)(—NRR)$_2$), carboxylate (—C(O)O$^-$), and others.

"Molecular diameter" refers to the diameter of the sphere of gyration of a polymer, which is a physical measure of the size of a molecule, and is defined as two times the mass weighted average distance from the core of a molecule to each mass element in the molecule. Stokes diameter or hydrodynamic diameter reflects the dimension of a molecule plus its associated water molecules as it moves through an aqueous solution, and is defined as the radius of an equivalent hard sphere diffusing at the same rate as the molecule under observation.

The term "polymer" refers to any molecule composed of more than three monomeric subunits.

The term "PLGA" or poly(lactic-co-glycolic acid) includes a copolymer which is biodegradable and biocompatible, and has the following structure:

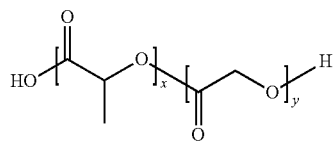

wherein x and y are independently selected from 1 to 5000. PLGA is commercially available at various ratios such as 85:15, 75:25, 65:35, 50:50, etc. Depending on the ratio of lactide to glycolide used for the polymerization, different forms of PLGA can be obtained. These are identified in regard to the molar ratio of the monomers used (e.g. PLGA 75:25 identifies a copolymer whose composition is 75% lactic acid and 25% glycolic acid). The crystallinity of PLGAs will vary from fully amorphous to fully crystalline depending on block structure and molar ratio. PLGAs typically show a glass transition temperature in the range of 40-60° C. PLGA can be dissolved by a wide range of solvents, depending on composition.

PLGA can be synthesized by means of ring-opening co-polymerization of two different monomers, the cyclic dimers (1,4-dioxane-2,5-diones) of glycolic acid and lactic acid. Polymers can be synthesized as either random or block copolymers thereby imparting additional polymer properties. Common catalysts used in the preparation of this polymer include tin(II) 2-ethylhexanoate, tin(II) alkoxides, or aluminum isopropoxide. During polymerization, successive monomeric units (of glycolic or lactic acid) are linked together in PLGA by ester linkages, thus yielding a linear, aliphatic polyester as a product.

Both L- and DL-lactides can be been used for co-polymerization. The ratio of glycolide to lactide at different compositions allows control of the degree of crystallinity of the polymers. When the crystalline PGA is co-polymerized with PLA, the degree of crystallinity is reduced and as a result this leads to increases in rates of hydration and hydrolysis. It can therefore be concluded that the degradation time of the copolymer is related to the ratio of monomers used in synthesis. In general, the higher the content of glycolide, the quicker the rate of degradation. However, an exception to this rule is the 50:50 ratio of PGA:PLA, which exhibits the fastest degradation.

DETAILED DESCRIPTION

The invention pertains to devices, methods and compositions for extended release of beneficial substances such as therapeutic agents. In some embodiments of the invention, the devices are implantable devices. In some embodiments, the compositions comprise a beneficial substance as well as a stability enhancing agent for the beneficial substance. In some embodiments, the stability enhancing agent provides long-term stability through an extended release mechanism such as through an erodible process (e.g., biodegradable polymer). In preferred embodiments of the invention, release of the beneficial substances is extended over at least one month. In more preferred embodiments of the invention, the release is extended over at least three months, 4, 5, 6, 7, 8, 9, 10, 11, or at least 12 months. In some embodiments, the equilibrium solubility of the beneficial substances in water, measured at room temperature, is more than about $1\times10^{-3}$ M.

In one embodiment, the present invention provides a composition that provides a "microenvironment" in the capsule of a drug delivery implantable device that increases or enhances the stability of the therapeutic agent. In some preferred embodiments, the stability enhancing composition is dry when implanted in a device and thereafter, admixes with interstitial body fluids for dissolution. The presence of at least one stability enhancing agent such as a biodegradable polymer, antioxidants, free radical scavengers, antimicrobial agents, or combinations thereof maintains the microenvironment compatible for the therapeutic agent, such as a protein or peptide agent by enhancing its stability and retaining the activity of the protein or peptide.

In one aspect, the stability enhancing agent is a biodegradable polymer that slowly breaks down for example, by hydrolysis to generate degradants such as lactic acid and or glycolic acid, which serve to maintain the microenvironment of the device with an acidic pH. The acidic pH enhances stability of the protein or peptide.

Further, a steady-state can exists between the degradants being released from the reservoir of the implantable device and the hydrolysis of the polymer. Further, other slightly soluble substances can be released and dissolved in a steady-state process.

In some embodiments, devices of the invention have a reservoir containing a composition of a therapeutic agent, and at least one membrane configured to achieve the extended release by controlling the rate of release of the therapeutic agent from the reservoir. In some embodiments the membrane controlling the rate of release of the therapeutic agent is a nanoporous membrane, i.e., a membrane with a porous structure wherein at least some of the pores form open, sub-micron, fluid-fillable pathways for the diffusion of molecular species through the membrane. In certain aspects, there are two or more membranes in the device. The nanoporous membrane can be a nanotube membrane. For example, the nanoporous membrane can be a nanotube membrane such as a titania nanotube membrane.

In some embodiments the pores in the membranes are nanochannels, such as those disclosed in U.S. Pat. No. 8,480,637 incorporated herein by reference. In some embodiments, the pores in the membranes are nanotubes, such as those disclosed in U.S. Patent Application Pub. No. 2014/0371687 incorporated herein by reference.

In some embodiments, the release rate of the therapeutic agent is controlled by matching the dimensions of the pores in the nanoporous membrane to the molecular dimensions or the hydrodynamic dimensions of the therapeutic agent.

In some embodiments, the smallest dimension of the pores is not more than 5 times a molecular dimension or hydrodynamic dimension of the therapeutic agent. In some embodiments, the smallest diameter of the pores is not more than 6, 7, 8, 9, 10, 11, or 12 times a molecular dimension or hydrodynamic dimension.

In some embodiments, compositions of the invention comprise a beneficial substance, such as a therapeutic agent and a stability enhancing agent for the beneficial substance, wherein the stability enhancing agent provides long term stability through an extended release mechanism of the stability enhancing agent (e.g., an erodible or biodegradable polymer).

In some embodiments, compositions of the invention are disposed within a reservoir of a nanotube membrane-controlled extended release dosage form, wherein the nanotube membrane is configured to achieve extended release of the therapeutic agent from the reservoir of a device.

In some embodiments, more than 1 beneficial substance such as a therapeutic agent is contained within the reservoir. In some embodiments, more than 1 stability enhancing agent is contained within the reservoir.

In some embodiments, the therapeutic agent is a protein or peptide. In the context of this disclosure, "peptides or proteins" refers to oligomers or polymers of at least 2 amino acid residues. The amino acids may be any type of amino acid, including natural and synthetic amino acids.

In some embodiments, suitable peptides include, but are not limited to beta-glucocerobrosidase, interferon alpha, interferon beta, agasidase alpha, agasidase beta, exenatide, octreotide, LHRH, LHRH analogs, calcitonin, nutropin/somatropin, factor VIII, aldesleukin, forigerimod, NP fusion proteins, IL-12, a melanocyte stimulating hormone, and bapineuzumab.

In some embodiments, the protein or peptide therapeutic agents are Glucagon-Like Peptide-1 receptor agonists also known as GLP-1 receptor agonists. In some embodiments, the GLP-1 receptor agonist is exenatide. In certain instances, exenatide has CAS No. 141732-76-5 and an empirical formula of $C_{184}H_{282}N_{50}O_{60}S$.

In preferred embodiments, the amount of exenatide can be from about 60 µg to about 50 mg, such as 100 µg, 200 µg, 300 µg, 400 µg, 500 µg, 600 µg, 700 µg, 800 µg, 900 µg, 1 mg, 10 mg, 20 mg, 30 mg, 40 mg, or 50 mg.

Many therapeutic agents, and especially protein- or peptide-based therapeutic agents are prone to degradation reactions such as oxidation, deamidation, racemization, and the like, as well as to irreversible aggregation and precipitation.

Such degradation reactions are often accelerated by the presence of water in a peptide or protein formulation. Some implantable peptide or protein delivery systems, such as osmotic pumps described in U.S. Pat. No. 8,052,996, incorporated herein by reference, comprise a flow modulator in the form of an elongated spiral channel, designed to keep water out of a formulation to be delivered by the osmotic pump. Some embodiments of the present invention, being diffusion-based systems, by definition need the substances to be delivered to be in solution. In some embodiments, those solutions are "created" by uptake of interstitial fluid upon implantation of the device in the body of a patient. Some formulations of the invention therefore face the challenge of requiring uptake of water for the device to be functional, while at the same time the presence of water may accelerate degradation reactions of the substances, like peptides and proteins, to be delivered.

In many instances, such degradation reactions can be reduced or prevented by stability enhancing agents such as acids, bases, anti-oxidants, free-radical scavengers, and the like. However, in some instances, the stability enhancing agents are significantly smaller than the therapeutic agents and the rate of release of the therapeutic agent through a membrane of a device is significantly slower than the rate of release of the stability enhancing agent, leading to premature depletion of the stabilizer.

Anti-oxidants can include natural anti-oxidants, such as carotenoids, vitamin E and vitamin C, and synthetic anti-oxidants, like butylated hydroxytoluene, butylated hydroxyanisol and propyl gallate.

For instance, in devices using a nanotube membrane the rate of release of a therapeutic agent from the reservoir may be controlled by matching the dimensions of the nanotubes to molecular dimensions or hydrodynamic dimensions of the therapeutic agent in such a manner that an extended release rate profile is achieved. However, when the therapeutic agent requires a stability enhancing agent, the dimensions of stabilizer molecules rarely match the dimensions of the therapeutic agent molecules, resulting in unmatched release of the two components. In the case of protein or peptide therapeutic agents, the stability enhancing agents are almost always significantly smaller than the therapeutic agent molecules, leading to rapid depletion of the stabilizer from the reservoir. Some embodiments of the present invention provide devices and compositions to overcome the problem of unmatched release rates of therapeutic agent molecules and stability enhancing agents from a device.

In some embodiments, the devices comprise a composition that that includes a beneficial substance, such as a therapeutic agent, as well as one or more stability enhancing agents, wherein the stabilizers provide long term stability through an extended release mechanism. In some embodiments, the extended release mechanism is biodegradation. Such extended release mechanisms may include, for instance, degradable polymeric forms of the stability enhancing agent i.e., stabilizer, formulations of low solubility forms of the stabilizer, stabilizers formulated into slow release micro-formulation, or stabilizers formulated into a membrane-encapsulated formulation. The terms polymer and oligomer are often used in a somewhat overlapping sense, and refer to molecules composed of multiple monomeric building blocks or subunits. Polymer, in this disclosure, collectively refers to any molecule composed of more than three monomeric subunits.

In preferred embodiments, the compositions are non-aqueous formulations, such as a dry powder formulations or suspensions of dry powders in a non-solvent liquid. Upon hydration, for instance, after implantation of the device comprising the composition at a desired location in the body of a subject, components of the formulation may start to dissolve and the stability enhancing agents i.e., stabilizers may become available in active form and at a functionally effective concentration. The functionally effective concentration may depend on the dosage form, on the type of stabilizer and/or on the therapeutic agent in the formulation.

In some embodiments, the functionally effective concentration of the stability enhancing agents may be extremely low.

For instance, for therapeutic agents that require a maximum pH of 6 to be stable, the functionally effective concentration of an acidic stabilizer only needs to produce a $H^+$ concentration of $10^{-6}$ mole/liter.

For instance, butylated hydroxytoluene (BHT) has a reported solubility of about 1 ppm in water, yet may be used as an effective low-solubility anti-oxidant in embodiments of the invention.

Embodiments of the invention further comprise methods to achieve extended release of beneficial substances from a device with a reservoir containing a formulation of the beneficial substance and having a nanoporous membrane configured to achieve the extended release of the therapeutic agent. Methods of the invention include a step of providing a stability enhancing agent, wherein the stability enhancing agent provides long term stability through an extended release mechanism of an erodible polymer.

Devices and methods using polymers based on lactic acid and glycolic acid as solubility modifying agents for sparingly soluble therapeutic agents have been disclosed in U.S. Patent Application Pub. No. 2011/0106006 incorporated herein by reference, wherein a therapeutic agent is defined as "relatively insoluble in water" or "sparingly soluble in water" if its equilibrium solubility in water, measured at room temperature, is less than about $1\times10^{-3}$ M.

Devices and methods of the present invention are using polymers based on lactic and glycolic acid as stabilizers in an extended release configuration, for the purpose of stabilizing therapeutic agents, and are applicable to therapeutic agents with any level of solubility in water.

In some embodiments, the compositions comprise stability enhancing agents which include biodegradable polymers. The stabilizers are incorporated in the polymeric molecules, for instance as their monomeric building blocks. Biodegradable polymers of the invention include both fully biodegradable polymers and partially biodegradable polymers. Partially degradable polymers can include segments of a non-degradable nature, such as poly-ethylene glycol segments.

Controlled degradation of the polymeric molecules continually generates smaller molecular species (monomers or "n-mers", wherein n can be an integer of 1, 2, 3, 4, 5, 6, 7, etc) and expose reactive end groups that contribute to the stabilization of the therapeutic agent molecules. Since stabilizer molecules are still present in polymeric form, they may not be released, or are released at a much slower rate from the dosage form than the individual monomeric molecules would be, and sustained stabilization is achieved. In some cases, the polymeric forms are not water-soluble, and are not released at any appreciable rate. Low molecular weight degradation products, such as monomers, dimers and trimers may be water-soluble, and, once produced may be released from the dosage form.

Examples of biodegradable polymers include those having at least some repeating unit representative of at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred degradable or erodible polymers comprise at least some repeating units representative of polymerizing at least one of lactic acid, glycolic acid, lactide, glycolide, ethylene oxide and ethylene glycol.

Specifically, when acidic molecules are used as stability enhancing agents i.e., stabilizers, the acidic molecules can be provided in polymeric forms, such as, for example, poly-esters, poly-orthoesters, poly-phosphoesters, poly-amides and poly-anhydrides, or copolymers thereof. In some embodiments, polymeric forms of stabilizers possess at least segments of poly-esters, poly-orthoesters, poly-phosphoesters, poly-amides and poly-anhydrides. Degradation of these polymeric forms may generate increasing amounts of acidic end groups capable of compensating for the exchange of $H^+$ ions with positive ions from the environment of use.

Preferred embodiments of such formulations include embodiments using well-known and widely accepted forms of acid-containing polymers, such as poly-lactic acid, poly-glycolic acid, and copolymers of lactic and glycolic acid. A wide variety of homopolymers and copolymers of lactic acid and glycolic acid is known in the art, and variable parameters include, for instance, molecular weight, lactide-glycolide co-polymer ratio, various combinations of d or l forms of poly-lactide in the polymer, levels of crystallinity, the absence or presence of terminating ester groups, etc. All these parameters can be varied at will, for instance to achieve polymers with different degradation rates, and different polymers may be mixed in dosage forms of the invention to obtain formulations with different degradation profiles.

For instance, a stabilizer mix may be prepared by mixing equal parts of three polymers based on lactic acid and glycolic acid. A 50/50 copolymer of lactic acid and glycolic acid with a molecular weight of about 10 kD may be mixed with a 70/30 copolymer of lactic, glycolic acid with a molecular weight of about 50 kD, and a homopolymer of pure 1-lactic acid with a molecular weight of 100,000.

In one aspect, the co-polymer of lactic acid and glycolic acid is in a ratio of 99:1 to 1:99 of lactic acid to glycolic acid. For example, the co-polymer of lactic acid and glycolic acid is in a ratio selected from the group of 85:15, 75:25, 65:35, 50:50 and 45:55.

In one aspect, the co-polymer of lactic acid and glycolic acid has a molecular weight of about 4000 to about 50,000. For example, the co-polymer of lactic acid and glycolic acid has a molecular weight of about 6000 to about 30,000 or the co-polymer of lactic acid and glycolic acid has a molecular weight of about 7000 to about 20,000.

In one aspect, the co-polymer of lactic acid and glycolic acid is in a weight ratio of 0.1-100:1 of the therapeutic agent. For example, the co-polymer of lactic acid and glycolic acid is in a weight ratio of 0.1-10:1 of the therapeutic agent.

The exact rates of degradation and generation of acidic groups may depend on the dosage form, and on the rate of release of the generated acids, but generally the mixture 50/50 copolymer will degrade within 4-6 weeks, the 70/30 copolymer in the 3-6 month time frame, while the pure homopolymer may last up to 1 year.

Even more extended degradation periods can be achieved by using a crystalline form of a pure L-lactic acid homopolymer.

The degradation rate of the pure homopolymer in the example above may be too slow to provide enough acidity in the early stages, hence the inclusion of more rapid degrading polymer species. Many variations on this theme are possible, for instance the use of different molecular weight fractions of pure poly-lactic acid, or the inclusion of additional components in the formulation. Those with ordinary skills in the art of bio-erodible polymer formulations will have no problems identifying such variations.

For instance, if desired, in some embodiments a "starter" species of acid may be included to accelerate the initial degradation of a lactide-co-glycolide polymer. For instance, benzoic acid has a limited solubility of about 0.5% in water at 37° C., and can create a pH between 2 and 3 in solution at that temperature. A pH at that level will accelerate the initial degradation of the lactide-co-glycolide polymer to create a faster initial generation of acidic polymeric or oligomeric species.

Therefore, a mixture of 1 part benzoic acid and 3 parts of a 70/30 copolymer of lactic, resp. glycolic acid with a molecular weight of about 50 kD may be prepared.

The acidity of the benzoic acid provides an initial stabilization for a therapeutic agent, while at the same time initiating a more rapid degradation of the copolymer, thereby obviating the need for a more rapidly degrading copolymer. Additionally, as will be described below, benzoic acid itself, because of its limited solubility can serve as a slow release stabilizer for acid-stabilized therapeutic agents as well.

In some exemplary embodiments, the stability enhancing agents (e.g., stabilizers) are provided as solid forms of substances with limited solubility in the solution that develops upon entry of interstitial fluid into the reservoir of the device after implantation in a subject. In some preferred embodiments, the solubility of the solid forms of the stabilizer provide when implanted a stabilizer solution with a concentration of less than 5% (weight/volume) inside the reservoir of a dosage form after administration to a subject (e.g., less than 0.1, 0.2, 0.3, 0.4, 0.5, 0.6, 0.7, 08, 0.9, 1.0, 2, 3, 4, 5%).

In some preferred embodiments, the solubility of the solid forms of the stabilizer is configured to provide a stabilizer solution with a concentration of less than 20% of the concentration of the therapeutic agent inside the reservoir of a dosage form after administration to a subject.

In some embodiments, the stability enhancing agents i.e., stabilizers will dissolve to a limited extent in the formulation solution inside a reservoir, and the dissolved form will be released from an extended release device at a rate that is limited by the solubility of the stabilizer. At the same time, because of the presence of excess solid form of the stabilizer, more of the stabilizer will dissolve as the previously dissolved molecules are being released, and a steady state of stabilizer concentration that is functionally effective to stabilize a beneficial agent in the reservoir may develop as a consequence of a balance between dissolution rate and release rate of the stabilizer.

In these embodiments the stabilizers can simply be added to the formulation, with no further treatment or formulation efforts, for instance by mixing powders of the stabilizers with powders of the therapeutic agents.

For instance, in order to maintain an acidic environment, low solubility acids may be used in formulations of the invention. The invention itself does not put any a priori limitations on the type of acid to be used. Inorganic acids and organic acids can be used, including saturated and unsaturated fatty acids, amino acids and naturally occurring and synthetic acids.

In some embodiments, other components of a specific formulation may determine the suitability of a range of available acids. For instance, a formulation including a solution of benzoic acid at 37° C. can have a pH between 2 and 3, while a similar formulation with stearic acid instead of benzoic acid may have a pH between 5.5 and 6. Formulations including a therapeutic agent which is stable between pH 4 and 6 would preferably be acidified with stearic acid and not with benzoic acid. Those with ordinary skills in the art of formulation development for therapeutic agents will be able to select suitable low solubility acidic compounds to match the stability requirements of the therapeutic agent without any undue experimentation.

Once implanted, the pH of the solution inside the capsule ("the microenvironment") can be acidic, i.e., less than 7. When the compositions are acidic, the pH of the compositions can be less than 7, or a pH of from about 2 to 7, or from about 3 to 7, or from about 4 to about 6. In some embodiments, the pH of the composition can be less than 7. In some embodiments, the pH of the composition can be from about 3.5 to 7. In some embodiments, the pH of the composition can be from about 4.5 to about 6.

In some embodiments, the therapeutic agent provides therapy from 30 days to about 1 year.

In some embodiments, the pH of the composition when admixed with interstitial fluid is from about 2 to 7 or from about 4 to about 6.

In some embodiments, the biodegradable polymer maintains a pH from about 3 to about 7 for a period of time such as about 30 days to about 1 year, for example, for a period of time of at least about 30 days after implantation of the device into a subject.

In an entirely analogous fashion, low solubility basic stabilizers may be selected. Basic stabilizers can include inorganic as well as organic bases, and naturally occurring and synthetic compounds. Preferred organic bases include primary, secondary, tertiary and quaternary amines.

In some exemplary embodiments, the stabilizers are provided in a separate extended or controlled release formulation. Many extended or controlled release technologies have been described in the art, in the form of scientific articles as well as in the form of handbooks, such as the Handbook of Pharmaceutical Controlled Release Technology 1st Edition, by Donald L Wise. Those with ordinary skills in the art of controlled release formulations will find a wide variety of suitable technologies for incorporation of stabilizers in the available literature. Embodiments of the invention using controlled release technologies for stabilizers have a broader scope of potentially suitable stabilizers, since the suitability of the stabilizers would no longer be determined by a degradation rate or a limited solubility. For instance, if higher solubility acids or bases were found to desirable, a controlled release formulation of such stabilizers may be prepared.

One group of technologies applicable to use in devices and dosage forms of the invention is based on micro formulations. In the context of this disclosure, micro-formulations refers to sub-millimeter particulate extended release formulations, such as extended release microparticles or microcapsules. The preparation of such controlled release microparticles and microcapsules is well known and has been practiced for many decades. A wide variety of technologies is available and has been described in the literature. (E.g. Jyothi, N V N et al., Microencapsulation techniques, factors influencing encapsulation efficiency, Journal of Microencapsulation, 2010; 27(3): 187-197 incorporated herein by reference).

Another type of technology applicable for use in devices and dosage forms of the invention larger than 1 millimeter is based on membrane-encapsulation of solid forms of stabilizers by a release rate controlling membrane. As long as the dissolving stabilizer inside the membrane maintains a saturated stabilizer solution, an extended, constant rate of release of the stabilizer through the membrane may be maintained.

In some embodiments, a combination of formulation elements described above may be used. For instance, a mixture of a degradable polymer and a slowly dissolving solid may be used. In such embodiments a degradable polymer with a very slow degradation rate may be used in combination with a solid with an intermediate dissolution rate. The solid may be used for short- to intermediate term stabilization, while the polymer provides the long-term duration of the stabilization period. Additionally, dissolution of the solid may control the degradation rate of the polymer, for instance when the dissolving solid "kick-starts" the degradation of the polymer. An example would be a mixture of a polymer of the poly-lactic-co-glycolide family with benzoic acid.

In another approach, a beneficial substance, such as a therapeutic agent, may be encapsulated in a polymer composed of stabilizing monomer units.

An example would be the encapsulation of an acid-stabilized therapeutic agent in a polymer of the poly-lactic-co-glycolide family. Encapsulation of many therapeutic agents in this family of polymers has been described, including encapsulation of water-soluble therapeutic agents and protein- and peptide based therapeutic agents. An advantage of this type of encapsulation is that a single powder formulation can be prepared of the final formulation, facilitating filling of a reservoir-based device or dosage form.

Other examples of stabilizers suitable for embodiments of the invention include anti-oxidants and free radical scavengers, anti-microbials, metal ions, protein cluster reducing agents such as surfactants, urea and guanidinium chloride, and protein cluster promoting agents like carbohydrates. These stabilizers can be formulated into extended release configurations using the same type of technologies as described above.

For instance, low solubility anti-oxidants and free radical scavengers, such as tocopherols, carotenoids, lipophilic flavonoids, butylated hydroxy toluene and propyl gallate may be incorporated in pure form into a formulation. In cases where higher solubility anti-oxidants and free radical scavengers, such as ascorbic acid, methionine, or glutathione are desired, their use may be rendered feasible in a controlled release technology configuration.

For instance, if an anti-microbial stabilizer is used, chlorhexidine can be used in a number of different configurations. As a free base, chlorhexidine is a low solubility stabilizer, and could serve the double purpose of being a basic stabilizer as well as an antimicrobial, and can be used as a simple powder. In some formulations it can be used in a pure powder form. If a more acidic environment is required, a salt form of chlorhexidine, like a gluconate, can be incorporated in a microparticle formulation based on copolymers of lactic and glycolic acid (PLGA). The microparticle formulation will provide an extended availability of acid groups, as well as provide an extended release of the chlorhexidine gluconate.

In some instances, especially in embodiments comprising peptide- or protein based therapeutic agents, the clustering or aggregation behavior of the peptides and proteins may affect their stability. In some cases, especially with larger proteins, clustering or aggregation may lead to the formation of irreversible aggregates, and inactivation of the protein. In other cases, for instance with some formulations of peptides, clustering of the molecules has been observed to stabilize the peptide against a number of degradation reactions. Therefore, promotion or reduction of clustering or aggregation tendencies may be an important aspect of formulation development. Typical anti-clustering agents include many compounds that tend to disrupt the internal hydrogen-bond based structure of water, such as surfactants, including ionic surfactants such a long chain fatty acid salts, and non-ionic surfactants such as the Tween, Brij and Triton series, and compounds like urea and guanidinium chloride. Formulation of any of these agents into a micro-formulation based on PLGA, like a PLGA microsphere formulation would provide a stabilizer formulation that would maintain an acidic environment based on the degradation of the PLGA, which is favorable for most peptides and proteins, as well as an extended availability of anti-clustering agents.

Clustering of peptides into stabilized supra-molecular aggregates is often promoted by carbohydrates, and especially by mono-saccharides and di-saccharides, such as many sugars. Use of the methods described above to produce slow release formulations of such carbohydrates may provide an extended availability of pro-clustering agents.

In some embodiments, compositions of the invention comprise metal ions. Metal ions have been found to stabilize certain protein molecules, such as the stabilization of human growth hormone with divalent metal ions, for instance zinc, cobalt and copper, or the stabilization of insulin with divalent metal ions like zinc.

Such metal ions may be provided as low solubility salts, such as phosphate salts, or as water-soluble salts, such as chloride forms, in an encapsulated form.

Some embodiments of the invention comprise formulations with additional ingredients, such as those described in EP 11 310 89 incorporated herein by reference or stabilization of insulin and in U.S. Pat. No. 5,766,582 incorporated herein by reference for the stabilization of interferon. Many of such stabilizers are available and have been described in the literature, and many approaches are available in the pharmaceutical art to create extended availability configurations. The total duration of the extended release may be determined on case-by-case basis for embodiments of the invention. Factors that may be taken into consideration include acceptable size of an implantable embodiment, acceptable levels of degradation of a therapeutic agent, required daily dose of the therapeutic agent, etc.

For instance, as was disclosed above, a combination of a 50/50 copolymer based on lactic and glycolic acid residues with a 30/70 copolymer and a polymer of pure L-lactic acid may be used to prepare a stabilizer formulation that provides an acidic environment for up to 1 year.

Embodiments comprising nanotube based membranes such as those disclosed in US Patent Application Pub. 2014/0371687, filed on Dec. 5, 2012 incorporated herein by reference, provides a technology for extended stabilization of therapeutic agents, because in addition to controlling the release of the therapeutic agents, they limit the uptake of damaging substances like oxygen.

The final formulations may have any desired configuration, such as dry formulations, including powder mixes and tabletted or compressed forms, and liquid mixtures, including solutions, suspensions and emulsions. Preparation of such configurations can be achieved with standard methods and equipment commonly used in the industry, including the pharmaceutical industry. The formulations are not limited to the use of a single stabilizer, and, in fact many preferred formulations will include a plurality of stabilizers, which may be provided in a variety of the extended release configurations described in this disclosure.

Those with ordinary skills in the art of formulation development of pharmaceutical dosage forms will be able produce embodiments of the invention based on this disclosure without undue experimentation.

For instance, the upper and lower limits for the amount of stabilizer to be used in embodiments of the invention can be determined on a case-by-case basis. The lower limit will typically be based on requirements of effectiveness, while the upper limit may be based on non-chemical considerations, such as the maximum clinically acceptable dimensions of a dosage form.

The lower limit can in part be determined through calculations or estimates of the rate leaching of stabilizer molecules from the device, or the rate of uptake of damaging molecules such as oxygen, or they can be determined through simple experimentation.

For instance, an embodiment of a device according to the invention with a reservoir and nanotube membrane based on titania nanotubes can be used in an incubation study with various experimental formulations. Table 1 below summarizes a number of formulations that can be used in combination with the device. The choice of a particular formulation can be determined based on additional considerations, such as intended duration, manufacturing history, use of terminal sterilization methods such as e-beam or gamma radiation, etc.

In order to assess the adequacy of the composition to stabilize the peptide for the intended application, the device with the formulation can be incubated in a relevant incubation medium, for instance a simulation of interstitial fluid like Phosphate Buffered Saline (PBS) at pH 7.4, and the released peptide and degradation products can be analyzed by High Pressure Liquid Chromatography (HPLC). Simultaneously, release of stabilizer molecules can be followed to assessing their retention in the. Additionally, at regular intervals, devices can be sacrificed and their internal contents analyzed by HPLC and visual observation. Based on the analytical results, the composition of the formulation can be adjusted as needed.

In Table 1 below examples are illustrated of composition adjustments around a formulation of exenatide as the therapeutic agent. Exenatide is merely provided as a model agent to illustrate steps in formulation development that are representative of steps undertaken in the development of formulations of the invention.

TABLE 1

| FUNCTION | IDENTITY | AMOUNT | PROPERTIES |
|---|---|---|---|
| Basic Formulation (Short Duration) | | | |
| Therapeutic Agent: | Exenatide | 7.5 mg | |
| Acidic Stabilizer | PLGA (lactic:Glycolic ratio 50:50, Mw 10,000) | 3-6 mg | 1-3 months duration of degradation |
| Basic Formulation (Long Duration) | | | |
| Therapeutic Agent: | Exenatide | 30 mg | |
| Acidic Stabilizer | PLGA (lactic:Glycolic ratio 50:50, Mw 10,000) | 2 mg | 1-3 months duration of degradation |
| | PLGA (Lactic:Glycolic ratio 70:30, Mw 50,000) | 2 mg | 3-6 months duration of degradation |
| | PLA Mw 100,000 | 3 mg | 6-12 months duration of degradation |
| Formulation (Short Duration) with added anti-oxidant/free radical scavenger | | | |
| Therapeutic Agent: | Exenatide | 7.5 mg | |
| Acidic Stabilizer | PLGA (lactic:Glycolic ratio 50:50, Mw 10,000) | 3-6 mg | 1-3 months duration of degradation |
| Anti-Oxidant: | BHT | 1-2 mg | Slow dissolving low concentration anti-oxidant |
| Formulations where low pH and high anti-oxidant levels are desired in a fast-dissolving setting, in addition to longer lasting stabilizers | | | |
| Therapeutic Agent: | Exenatide | 7.5 mg | |
| Acidic Stabilizer | PLGA (lactic:Glycolic ratio 50:50, Mw 10,000) | 3-6 mg | 1-3 months duration of degradation |
| Anti-Oxidant/ free radical scavenger | BHT | 1-2 mg | Slow dissolving low concentration anti-oxidant and free radical scavenger |

TABLE 1-continued

| FUNCTION | IDENTITY | AMOUNT | PROPERTIES |
|---|---|---|---|
| Acidic anti-oxidant | Methionine | 3-6 mg | Fast dissolving acidic anti-oxidant. Rapidly produces low pH and anti-oxidative solution. Released relatively quickly. |
| Formulations where higher concentrations of long lasting anti-oxidant/free radical scavengers are desired | | | |
| Therapeutic Agent: | Exenatide | 7.5 mg | |
| Acidic Stabilizer | PLGA (lactic:Glycolic ratio 50:50, Mw 10,000) | 3-6 mg | 1-3 months duration of degradation |
| Anti-Oxidant: | BHA | 3-6 mg | Slightly higher solubility than BHT. Produces higher level of stabilizer, but is released faster |
| Formulation (Long Duration) with added anti-oxidant/free radical scavenger | | | |
| Therapeutic Agent: | Exenatide | 30 mg | |
| Acidic Stabilizer | PLGA (lactic:Glycolic ratio 50:50, Mw 10,000) | 2 mg | 1-3 months duration of degradation |
| | PLGA (Lactic:Glycolic ratio 70:30, Mw 50,000) | 2 mg | 3-6 months duration of degradation |
| | PLA Mw 100,000 | 3 mg | 6-12 months duration of degradation |
| Anti-Oxidant: | BHT | 3-6 mg | Slightly higher solubility than BHT. Produces higher level of stabilizer, but is released faster |

Note:
Polymer Molecular Weight (Mw) in this disclosure refers to the weight average molecular weight.

As was mentioned above, embodiments of the invention can be especially useful for the stabilization of protein- and peptide based therapeutic agents. Specifically, some embodiments of the invention are useful for the stabilization of GLP-1 agonists, such as exenatide. Some formulations of exenatide according to the invention are especially suitable for use in membrane-controlled reservoir devices for extended release of the therapeutic agent. In some embodiments the membrane controlling the rate of release of the therapeutic agent is a nanotube membrane, i.e. a nanoporous membrane based on an array of nanotubes with a controlled porosity. In some embodiments the nanotube membrane is based on titania nanotubes, such as those disclosed in US Patent Application Pub. No. 2014/0371687, filed on Dec. 5, 2012 incorporated herein by reference.

Embodiments of the invention include formulations of exenatide with stabilizers formulated into an extended availability configuration, as well as devices for the extended release of exenatide from such formulations, including devices with nanotube based membranes.

Exenatide stability benefits from an acidic environment. Accordingly, stabilizers co-formulated with exenatide include acidic and acid-generating substances, such as PLGA. Additionally, exenatide may be stabilized by the addition of a low solubility anti-oxidants, such as Butylated Hydroxy Anisole (BHA) and Butylated Hydroxy Toluene (BHT).

The doses suitable for the treatment of diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

In certain embodiments, the exenatide concentration is sufficient to achieve an average or minimum circulating blood plasma level of exenatide of at least about 1 month, at least about 3 months, or at least about 6 months, at least about 8 months, at least about 12 months or even more.

II. DEVICE

A device useful in the present invention is disclosed in WO 2015/112811 incorporated herein by reference, which has a nanoporous membrane. The device comprises a capsule suitable for implantation, a reservoir encapsulated by the capsule, wherein the reservoir is suitable for containing a therapeutic agent, and a nanopore membrane attached to the capsule such that the nanopore membrane is in contact with the reservoir, wherein the nanopore membrane includes a plurality of nanopores in fluid contact with the reservoir, wherein the nanopores have an interior with optionally a coating layer on at least a portion of the interior, such that the plurality of nanopores is a diffusion pathway out of the reservoir for the therapeutic agent.

The capsule (100) of the FIGURE can be any capsule that is biocompatible with the body. The capsule can be prepared from any suitable material such as metals, polymers and combinations thereof. Useful metals can be pure metals or alloys, and include, but are not limited to, titanium and steel. Polymers useful in the present invention include any natural or synthetic polymer that is biocompatible with the body. In some embodiments, the capsule includes titanium. The reservoir can be any suitable volume and dimensions sufficient to release the therapeutic agent at a constant rate for the given interval.

Typically, the device also includes the reservoir (110), which contains the therapeutic agent. Any therapeutic agent is useful in the device of the present invention. The therapeutic agent can be in any suitable form in the reservoir, such as a liquid, a solid or a suspension. Solid forms include, but are not limited to, powders and micronized particles. For example, the powder can be lyophilized.

The titanium substrate (130) of the FIGURE can be attached to the capsule by any suitable methods in the art. For example, the titanium substrate can be laser welded to the capsule.

The titania nanotubes (121) can have any suitable dimensions, including the internal diameter, the length and the aspect ratio. The internal diameter can be from about 1 nm to about 1000 nm, and can be the same or variable along the length of the titania nanotube. When the internal diameter is variable, the internal diameter can increase from one end of the titania nanotube to the other. For example, the internal diameter of the titania nanotube at the end in contact with the reservoir can be smaller than at the end opposite the reservoir, where the internal diameter increases gradually along the length of the titania nanotube. The internal diameter can be about 1, 2, 3, 4, 5, 6, 7, 8, 9, 10, 15, 20, 25, 50, 75, 100, 200, 300, 400, 500 or 1000 nm. The internal diameter can be of from about 1 to 1000 nm, or from about 1 to about 100 nm, or from about 1 to about 50 nm, or from about 1 to about 20 nm. In some embodiments, the internal diameter can be of from about 10 nm to about 1000 nm.

The titania nanotubes can have any suitable length. For example, the titania nanotubes can be from about 100 nm to about 100 μm, or about 500 nm, 1 μm, 5, 10, 20, 30, 40, 50, 60, 70, 80, 90 or 100 μm. In some embodiments, the titania nanotubes have a length of about 1 μm to about 100 μm.

The titania nanotubes can also have any suitable aspect ratio, defined by the length of the titania nanotube divided by the internal or external diameter. The aspect ratio can be from about 10 to about 10,000, or from about 10 to about 1,000. Other aspect ratios include, but are not limited to, about 50, 100, 200, 300, 400, 500, 600, 700, 800, 900, 1000, 2000, 3000, 4000, 5000, 6000, 7000, 8000, 9000, or 10,000.

The titania nanotubes are in fluid contact with the reservoir such that the therapeutic agent can diffuse from the reservoir and into the titania nanotubes at the titanium substrate, followed by exiting the titania nanotubes at the opposite end and entering the body. The rate of release of the therapeutic agent can be any suitable rate of release, such as zero-order rate of release. In some embodiments, the release of the therapeutic agent from the reservoir and through the titania nanotube membrane is a zero-order rate of release.

III. EXTENDED RELEASE EMBODIMENTS

In the embodiments below, the phrase "extended release configuration" means that the stability enhancing agent or stabilizer provides long-term stability through an extended release mechanism. Mechanisms include, but are not limited to, erosion, biodegradation of a polymer, dissolution, enzymatic cleavage, hydrolysis, proteolytic cleavage, and the like.

In one embodiment, the present invention provides a device for extended release of a beneficial substance, the device comprising:
a reservoir containing the beneficial substance and a stabilizer for the beneficial substance; and
a nanoporous membrane connected with the reservoir; wherein the nanoporous membrane is configured to achieve the extended release of the beneficial substance from the reservoir, and wherein the stabilizer for the beneficial substance is provided in an extended release configuration.

In one aspect, the nanoporous membrane is one of a nanotube membrane and a nanochannel membrane.

In one aspect, the nanoporous membrane in any of the preceding aspects, is a nanotube membrane based on titania nanotubes.

In one aspect, the extended release configuration in any of the preceding aspects, comprises a biodegradable polymer formulation configured to generate stabilizing functional groups upon degradation.

In one aspect, the extended release configuration in any of the preceding aspects, comprises a low solubility formulation of the stabilizer, configured to provide a solution with a functionally effective stabilizer concentration inside the reservoir during the extended release of the beneficial substance.

In one aspect, the functionally effective stabilizer in any of the preceding aspects, has a concentration of less than 5% (w/v).

In one aspect, the functionally effective stabilizer in any of the preceding aspects, has concentration less than 20% of a concentration of the beneficial agent in the solution.

In one aspect, the extended release configuration in any of the preceding aspects, comprises a micro-formulation of the stabilizer.

In one aspect, the extended release configuration in any of the preceding aspects, comprises a membrane-encapsulated form of the stabilizer.

In one aspect, the stabilizer in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer formulation in any of the preceding aspects, comprises at least one of a poly-ester, a poly-amide, a poly-anhydride, a poly-saccharide, a poly-orthoester, and a poly-lactone.

In one aspect, the biodegradable polymer formulation in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial substance in any of the preceding aspects, is exenatide.

In one embodiment, the present invention provides a device for controlled release of a beneficial substance, the device comprising:
a reservoir containing a formulation of the beneficial substance; and
a nanoporous membrane connected with the reservoir and configured to provide extended release of the beneficial substance from the reservoir;
the formulation comprising:
the beneficial substance;
a stabilizer for the beneficial substance; and
means to provide extended availability of the stabilizer for the beneficial substance.

In one aspect, the nanoporous membrane is one of a nanotube membrane and a nanochannel membrane.

In one aspect, the nanoporous membrane in any of the preceding aspects, is a nanotube membrane based on titania nanotubes.

In one aspect, the means to provide extended availability of the stabilizer for the beneficial substance in any of the preceding aspects, comprises a biodegradable polymer formulation configured to generate stabilizing functional groups upon degradation.

In one aspect, the means to provide extended availability of the stabilizer for the beneficial substance in any of the preceding aspects, comprises a low solubility formulation of the stabilizer, configured to provide a solution with a functionally effective stabilizer concentration inside the reservoir during the extended release of the beneficial substance.

In one aspect, the functionally effective stabilizer concentration in any of the preceding aspects, is less than 5% (w/v).

In one aspect, the functionally effective stabilizer concentration in any of the preceding aspects, is less than 20% of a concentration of the beneficial agent in the solution.

In one aspect, the means to provide extended availability of the stabilizer for the beneficial substance in any of the preceding aspects, comprises a micro-formulation of the stabilizer.

In one aspect, the means to provide extended availability of the stabilizer for the beneficial substance in any of the preceding aspects, comprises a membrane-encapsulated form of the stabilizer.

In one aspect, the stabilizer for the beneficial substance in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer formulation in any of the preceding aspects, comprises at least one of a poly-ester, a poly-amide, a poly-anhydride, a poly-saccharide, a poly-orthoester, and a poly-lactone.

In one aspect, the biodegradable polymer formulation in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial substance in any of the preceding aspects, is exenatide.

In one embodiment, the present invention a method comprising the steps of:
providing a device with a reservoir and a nanoporous membrane, the membrane configured to achieve extended release of a beneficial substance from the reservoir and being connected with the reservoir;
providing a beneficial substance; and
providing a stabilizer for the beneficial substance;
wherein the stabilizer is provided in an extended release configuration.

In one aspect, the nanoporous membrane is one of a nanotube membrane and a nanochannel membrane.

In one aspect, the nanoporous membrane in any of the preceding aspects, is a nanotube membrane based on titania nanotubes.

In one aspect, the extended release configuration in any of the preceding aspects, comprises a biodegradable polymer formulation configured to generate stabilizing functional groups upon degradation.

In one aspect, the extended release configuration in any of the preceding aspects, comprises a low solubility formulation of the stabilizer, configured to provide a solution with a functionally effective stabilizer concentration inside the reservoir during the extended release of the beneficial substance.

In one aspect, the functionally effective stabilizer in any of the preceding aspects, has a concentration less than 5% (w/v).

In one aspect, the functionally effective stabilizer concentration in any of the preceding aspects, is less than 20% of a concentration of the beneficial agent in the solution.

In one aspect, the extended release configuration in any of the preceding aspects, comprises a micro-formulation of the stabilizer.

In one aspect, the extended release configuration in any of the preceding aspects, comprises a membrane-encapsulated form of the stabilizer.

In one aspect, the stabilizer in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer in any of the preceding aspects, comprises at least one of a poly-ester, a poly-amide, a poly-anhydride, a poly-saccharide, a poly-orthoester, and a poly-lactone.

In one aspect, the biodegradable polymer in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial substance in any of the preceding aspects, is exenatide.

In one embodiment, the present invention provides method comprising the steps of:
providing a device with a reservoir and a nanoporous membrane, the membrane configured to achieve extended release of a beneficial substance from the reservoir and being connected with the reservoir;
providing a beneficial substance;
providing a stabilizer for the beneficial substance; and
providing means for achieving extended availability of the stabilizer for the beneficial substance.

In one aspect, nanoporous membrane is one of a nanotube membrane and a nanochannel membrane.

In one aspect, the nanoporous membrane in any of the preceding aspects, is a nanotube membrane based on titania nanotubes.

In one aspect, the means to provide extended availability of the stabilizer for the beneficial substance in any of the preceding aspects, comprises a biodegradable polymer formulation configured to generate stabilizing functional groups upon degradation.

In one aspect, the means to provide extended availability of the stabilizer for the beneficial substance in any of the preceding aspects, comprises a low solubility formulation of the stabilizer, configured to provide a solution with a functionally effective stabilizer concentration inside the reservoir during the extended release of the beneficial substance.

In one aspect, the functionally effective stabilizer concentration in any of the preceding aspects, is less than 5% (w/v).

In one aspect, the functionally effective stabilizer concentration in any of the preceding aspects, is less than 20% of a concentration of the beneficial agent in the solution.

In one aspect, the means to provide extended availability of the stabilizer for the beneficial substance in any of the preceding aspects, comprises a micro-formulation of the stabilizer.

In one aspect, the means to provide extended availability of the stabilizer for the beneficial substance in any of the preceding aspects, comprises a membrane-encapsulated form of the stabilizer.

In one aspect, the stabilizer for the beneficial substance in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer formulation in any of the preceding aspects, comprises at least one of a poly-ester, a poly-amide, a poly-anhydride, a poly-saccharide, a poly-orthoester, and a poly-lactone.

In one aspect, the biodegradable polymer in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial substance in any of the preceding aspects, is exenatide.

In one embodiment, the present invention provides a formulation for extended release of a beneficial substance, the formulation being disposed within a reservoir of a nanotube membrane-controlled extended release dosage form, the nanotube membrane being configured to achieve extended release of the beneficial substance from the reservoir, the formulation comprising:
 the beneficial substance; and
 a stabilizer for the beneficial substance;
 wherein the stabilizer is provided in an extended release configuration.

In one aspect, nanoporous membrane is one of a nanotube membrane and a nanochannel membrane.

In one aspect, the nanoporous membrane in any of the preceding aspects, is a nanotube membrane based on titania nanotubes.

In one aspect, the extended release configuration in any of the preceding aspects, comprises a biodegradable polymer formulation configured to generate stabilizing functional groups upon degradation.

In one aspect, the extended release configuration in any of the preceding aspects, comprises a low solubility formulation of the stabilizer, configured to provide a solution with a functionally effective stabilizer concentration inside the reservoir during the extended release of the beneficial substance.

In one aspect, the functionally effective stabilizer concentration in any of the preceding aspects, is less than 5% (w/v).

In one aspect, the functionally effective stabilizer concentration in any of the preceding aspects, is less than 20% of a concentration of the beneficial agent in the solution.

In one aspect, the extended release configuration in any of the preceding aspects, comprises a micro-formulation of the stabilizer.

In one aspect, the extended release configuration in any of the preceding aspects, comprises a membrane-encapsulated form of the stabilizer.

In one aspect, the stabilizer in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer in any of the preceding aspects, comprises at least one of a poly-ester, a poly-amide, a poly-anhydride, a poly-saccharide, a poly-orthoester, and a poly-lactone.

In one aspect, the biodegradable polymer in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial in any of the preceding aspects, substance is exenatide.

In one embodiment, the present invention provides a formulation for extended release of a beneficial substance, the formulation being disposed within a reservoir of a nanotube membrane-controlled extended release dosage form, the nanotube membrane being configured to achieve extended release of the beneficial substance from the reservoir, the formulation comprising:
 the beneficial substance;
 a stabilizer for the beneficial substance; and
 means to provide extended availability of the stabilizer.

In one aspect, the nanoporous membrane is one of a nanotube membrane and a nanochannel membrane.

In one aspect, the nanoporous membrane in any of the preceding aspects, is a nanotube membrane based on titania nanotubes.

In one aspect, the means to provide extended availability of the stabilizer for the beneficial substance in any of the preceding aspects, comprises a biodegradable polymer formulation configured to generate stabilizing functional groups upon degradation.

In one aspect, the means to provide extended availability of the stabilizer for the beneficial substance comprises a low solubility formulation of the stabilizer, configured to provide a solution with a functionally effective stabilizer concentration inside the reservoir during the extended release of the beneficial substance.

In one aspect, the functionally effective stabilizer concentration in any of the preceding aspects, is less than 5% (w/v).

In one aspect, the functionally effective stabilizer concentration in any of the preceding aspects, is less than 20% of a concentration of the beneficial agent in the solution.

In one aspect, the means to provide extended availability of the stabilizer for the beneficial substance in any of the preceding aspects, comprises a micro-formulation of the stabilizer.

In one aspect, the means to provide extended availability of the stabilizer for the beneficial substance in any of the preceding aspects, comprises a membrane-encapsulated form of the stabilizer.

In one aspect, the stabilizer for the beneficial substance in any of the preceding aspects, comprises at least one of an acid, a base, an anti-oxidant, a free radical scavenger, an antimicrobial, a protein cluster promoting agent and a protein cluster reducing agent.

In one aspect, the biodegradable polymer in any of the preceding aspects, comprises at least one of a poly-ester, a poly-amide, a poly-anhydride, a poly-saccharide, a poly-orthoester, and a poly-lactone.

In one aspect, the biodegradable polymer in any of the preceding aspects, comprises at least one of a homo-polymer of lactic acid, a homo-polymer of glycolic acid and a co-polymer of lactic acid and glycolic acid.

In one aspect, the beneficial substance in any of the preceding aspects, comprises one of a peptide and a protein.

In one aspect, the beneficial substance in any of the preceding aspects, is exenatide.

IV. EXAMPLES

The following examples are offered to illustrate, but not to limit the claimed invention.

In a forced degradation study, exenatide was incubated with and without PLGA at 37 C for 8 weeks. To avoid confounding factors, no other stabilizers were used in the study. Solutions of 20% (w/v) of exenatide in Water For Injection with 0.04% $NaN_3$ to prevent bacterial growth were filled into 40 microliter titanium reservoirs, with or without the addition of 5 mg of PLGA in the reservoirs (PLGA; MW 7.000-17.000; Lactic acid:Glycolic acid 50:50). The reservoirs were closed using a titanium screw caps with a nanotube membrane according to US Patent Application Pub. No. 2014/0371687.

The devices were incubated in phosphate buffered saline (pH 7.4) under full access to air (oxygen). E-beam sterilized (25 k Gray) exenatide and PLGA were used as well as non-irradiated controls according to the Table 1.

At various time points the devices were switched from the PBS solution to a citric acid buffer at pH 5, and the exenatide released through the nanotubes membranes into the citric acid buffer was analyzed for purity using High Pressure Liquid Chromatography (HPLC). Citric acid buffer was used to stabilize the released exenatide, as exenatide degrades rapidly at pH 7.4.

The results are represented in Table 2.

TABLE 2

Compositions

| | Sample | | | |
|---|---|---|---|---|
| | 1 | 2 | 3 | 4 |
| Exenatide solution | 200 mg/ml | 200 mg/ml | — | — |
| Irradiated exenatide solution | — | — | 200 mg/ml | 200 mg/ml |
| PLGA | — | 5 mg | — | — |
| Irradiated PLGA | — | — | — | 5 mg |

TABLE 3

Exenatide purity over time (% purity)

| | Time (Days) | | | | | |
|---|---|---|---|---|---|---|
| Sample | 7 | 14 | 28 | 35 | 42 | 56 |
| Exenatide only | 99 | 89 | 87 | 82 | 72 | 62 |
| Exenatide only (Irradiated) | 96 | 91 | 82 | 75 | 66 | 51 |
| Exenatide + PLGA | 99 | 95 | 89 | 86 | 81 | 79 |
| Exenatide + (PLGA) Irradiated | 98 | 95 | 88 | 84 | 81 | 78 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An implantable drug delivery system, said implantable drug delivery system comprising:
   a titanium capsule suitable for implantation;
   a reservoir encapsulated by the capsule, at least one nanoporous membrane in fluid contact with the reservoir, wherein the reservoir contains a pharmaceutical composition including a water soluble therapeutic agent with an equilibrium solubility at room temperature of more than $1.0 \times 10^{-3}$M; and a stability enhancing agent, wherein the stability enhancing agent is a biodegradable polymer which generates an acidic molecule upon degradation.

2. The implantable drug delivery system of claim 1, wherein the therapeutic agent is a protein or peptide.

3. The implantable drug delivery system of claim 2, wherein the protein or peptide is selected from the group consisting of beta-glucocerobrosidase, interferon a, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab.

4. The implantable drug delivery system of claim 1, wherein the therapeutic agent is a member selected from the group consisting of exenatide and octreotide.

5. The implantable drug delivery system of claim 1, wherein the therapeutic agent is exenatide.

6. The implantable drug delivery system of claim 5, wherein the amount of exenatide is about 60 μg to about 50 mg.

7. The implantable drug delivery system of claim 1, wherein the biodegradable polymer is a member selected from the group consisting of a poly-ester, a poly-amide, a poly-anhydride, a poly-saccharide, a poly-orthoester, a poly-lactone and a combination thereof.

8. The implantable drug delivery system of claim 7, wherein the biodegradable polymer is a member selected from the group consisting of a homo-polymer of lactic acid, a homo-polymer of glycolic acid and a co-polymer of lactic acid and glycolic acid.

9. The implantable drug delivery system of claim 8, wherein the biodegradable polymer is a co-polymer of lactic acid and glycolic acid.

10. The implantable drug delivery system of claim 9, wherein the co-polymer of lactic acid and glycolic acid is in a ratio of 99:1 to 1:99 of lactic acid to glycolic acid.

11. The implantable drug delivery system of claim 9, wherein the co-polymer of lactic acid and glycolic acid is in a ratio selected from the group of 85:15, 75:25, 65:35, 50:50 and 45:55.

12. The implantable drug delivery system of claim 9, wherein the co-polymer of lactic acid and glycolic acid has a molecular weight of about 4000 to about 50,000.

13. The implantable drug delivery system of claim 9, wherein the co-polymer of lactic acid and glycolic acid has a molecular weight of about 6000 to about 30,000.

14. The implantable drug delivery system of claim 9, wherein the co-polymer of lactic acid and glycolic acid has a molecular weight of about 7000 to about 20,000.

15. The implantable drug delivery system of claim 9, wherein the co-polymer of lactic acid and glycolic acid is in a weight ratio of 0.1-100:1 of the therapeutic agent.

16. The implantable drug delivery system of claim 9, wherein the co-polymer of lactic acid and glycolic acid is in a weight ratio of 0.1-10:1 of the therapeutic agent.

17. The implantable drug delivery system of claim 1, wherein the pharmaceutical composition is a member selected from the group consisting of a solid, a powder, a granule, and a microsphere.

18. A method for treating a disease in a subject in need thereof, the method comprising:
   administering to the subject a therapeutically effective amount of a water soluble therapeutic agent, which has an equilibrium solubility at room temperature of more than $1.0 \times 10^{-3}$M contained within an implantable drug delivery system, the drug delivery system including:
   a titanium capsule suitable for implantation;
   a reservoir encapsulated by the capsule, at least one nanoporous membrane in fluid contact with the reservoir, wherein the reservoir contains a pharmaceutical composition comprising the therapeutic agent and a stability enhancing agent, wherein the stability enhancing agent is a biodegradable polymer which generates an acidic molecule upon degradation.

* * * * *